United States Patent [19]
Nagai

[11] Patent Number: 4,762,492
[45] Date of Patent: Aug. 9, 1988

[54] ARTIFICIAL TOOTH ROOT MEMBER AND METHOD OF IMPLANTING SAME

[75] Inventor: Noriyuki Nagai, Okayama, Japan

[73] Assignee: Yamaura Seisakusho Ltd., Tokyo, Japan; a part interest

[21] Appl. No.: 56,240

[22] Filed: Jun. 1, 1987

[30] Foreign Application Priority Data

Jul. 18, 1986 [JP] Japan .................... 61-170689

[51] Int. Cl.$^4$ ............................................. A61C 8/00
[52] U.S. Cl. ................................ 433/174; 433/176
[58] Field of Search .............. 433/173, 174, 175, 176, 433/201.1

[56] References Cited

U.S. PATENT DOCUMENTS 4,416,629 11/1983 Mozsary et al. ................ 433/173
4,713,003 12/1987 Symington et al. ............. 433/173

FOREIGN PATENT DOCUMENTS 2454414 5/1975 Fed. Rep. of Germany ...... 433/176

Primary Examiner—Carroll B. Dority, Jr.
Attorney, Agent, or Firm—Barnes, Kisselle, Raisch, Choate, Whittemore & Hulbert

[57] ABSTRACT

A screw element is brought in thread engagement with a blade-shaped piece having a first threaded hole and open at sides, and the piece and the screw element are implanted together in a jawbone. A newly grown jawbone goes into osteobond with the implanted piece and screw element, the jawbone thus defining a second threaded hole. Subsequently the screw element is removed, and a pin neck portion is threadedly fitted into position in place of the screw element. The piece is small in size and open at sides. Therefore, it has no unfavorable effect on adjacent teeth and can be steadily implanted in a narrow jawbone structure. The pin neck portion is securely fixed by both the first threaded hole of the piece and the bone-defined second threaded hole, being thus steadily implanted in position.

15 Claims, 8 Drawing Sheets

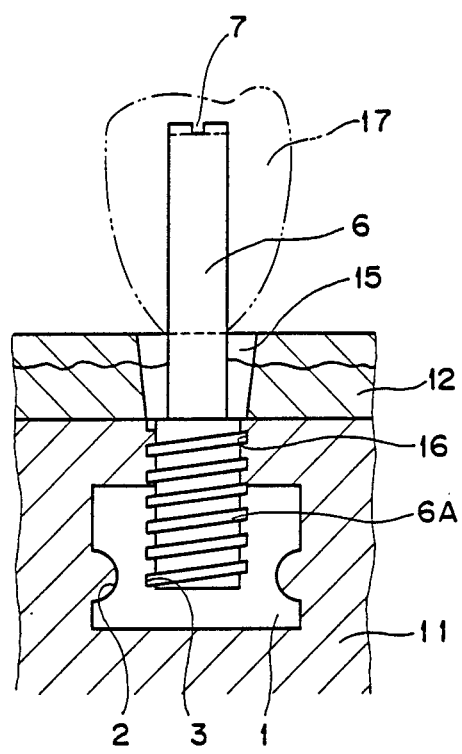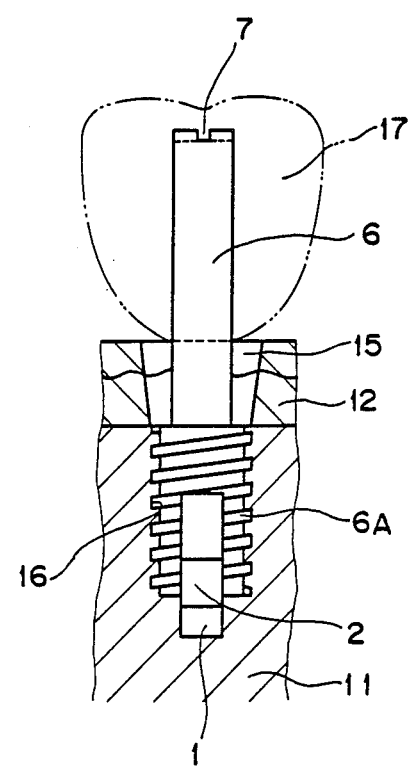

ARTIFICIAL TOOTH ROOT MEMBER AND METHOD OF IMPLANTING SAME

FIELD OF THE INVENTION

This invention relates to an artificial tooth root member for use in implanting an artificial tooth root in a jawbone and mucous structure by the so called built up technique (doule implanting technique), and a method of implanting same.

BACKGROUND OF THE INVENTION

The art of artificial tooth roots has a long history. Since as early as the 1930's, various attempts have been made for material development and improvement in configuration and implanting techniques. Various kinds of artificial tooth roots have hitherto been used including those made of metals (such titanium and Co - Cr alloy), alumina-ceramic, zirconia-ceramic, and sintered aphthite material. In configuration they are classified as screw type, hollow type, and blade type; and they have their respective merits and demerits. There are known two implanting methods, namely, single implanting method and double implanting method.

For the purpose of implanting an artificial tooth root in a jawbone and mucous structure and fixing it in position, it is today believed essential that if the artificial tooth root is to be long stabilized and kept in its implanted condition without being disturbed, there must be an early bonding between the artificial tooth root and the jawbone at their interface so that the osteobond is histologically fixed.

The condition for success in artificial tooth root implanting which has so far been made clear is that a good bond between the implanted portion of the artificial tooth root and the jawbone be achieved at an early point of time. Necessary factors for achievement of an osteobond include designing as to implanting procedure and configuration, and material selection. Most artificial tooth roots in use today relate to the single implant technique.

Artificial tooth roots of the screw type or the blade type, in which the pin neck portion is exposed in an oral cavity are used in conjunction with single implanting techniques in such a way that natural implantation is intended while the pin neck portion is kept in projection in the oral cavity to allow an osteobond. However, the difficulty is that occlusion with an opposite tooth is commenced before a sufficient bond is obtained between the implanted portion of the artificial root and the jawbone; therefore, some excessive pressure is exerted on the artificial tooth root during mastication, and inflammation is caused by lateral pressure due to tongue depression or by infection, it being thus impossible to obtain unstrained implantation, with the result of root shaking or falling off.

Another difficulty with such root implanted by single implant techniques is that just after extraction, the jawbone portion of the wound socket by which the root of a natural tooth root had been supported is a soft granulation tissue, and therefore that the artificial tooth root, if immediately planted in the socket, is easily disturbed and cannot be kept stable. Most artificial tooth roots known today are implanted after a post-tooth-extraction jawbone is well ossificated, but in this case the trouble is that since a jaw bank tends to shrink and absorb after teeth falling, it becomes gradually difficult to implant artificial tooth roots as ageing progresses. In this way, the single implanting technique involves many problems.

Therefore, if it is possible to employ a double implanting method such that a blade-type piece is first implanted in a jawbone and allowed to stand until an osteobond is completely formed between the blade type piece and the jawbone, and after completion of such bond a pin neck portion is implanted in the blade type piece, aforesaid problems can be solved. That is, in order to achieve good osteobond, it is desirable to employ a double implanting method wherein complete implantation is effected which provides freedom from disturbance.

An artificial tooth root which can be used with such double implanting technique is known, as typically found in Japanese Published Examined Patent Application No. 56-27262, wherein a piece implantable in a jawbone consists of a cylindrical portion and side arms, and wherein a fitting pin brought in thread engagement with a threaded hole defined in the cylindrical portion is disengagesd from the threaded hole, a pin neck portion being then brought into thread engagement with the threaded hole for implantation therein.

One drawback of this prior-art arrangement is that if the cylindrical portion is made diametrically large, it is difficult to implant it stably in a jawbone having a limited width, while on the other hand, if the cylindrical portion is made small in diameter, the threaded portion of a pin neck portion is made diametrically small correspondingly, it being thus unexpectable to obtain good strength enough to withstand any subtantial force resulting from occlusion with an opposite tooth. Another difficulty with the known arrangement, in which each side arm is formed with a slit to ensure strong osteobond with the jawbone, is that only with such slit it is difficult to expect any substantially strong osteobond. If an attempt is made to construct the side arm larger in order to obtain increased bond strength, it is impracticable to make the side arm to the required extent because of the presence of adjacent natural teeth or otherwise; and if the side arm is made large at all, it will have an adverse effect on adjacent teeth. Another difficulty is that the joint portion between the pin neck portion and an upper structure makes a filthy region of oral mucous membrane and is likely to invite inflammation.

SUMMARY OF THE INVENTION

Accordingly, the object of the invention is to provide an artificial tooth-root member and method of implanting same which uses a thin and small-sized blade type piece and yet provides strong osteobond with a jawbone, and which permits double implantation and allows the piece to be effectively implanted in a wound socket right after tooth extraction.

In order to accomplish this object, a first aspect of the invention comprises a blade-shaped piece implantable in a jawbone and having a first threaded hole open at sides, a screw element threaddedly engageable with the first threaded hole and serving for the purpose of forming a second threaded hole in the jawbone, and pin neck portion substitutable for the screw element and formed at the base end part thererof with a threaded portion engageable with the first and second threaded holes.

A second aspect of the invention comprises:
(a) cutting a groove around a socket after tooth extraction to form an implanting groove, (b) fitting into the implanting groove an implant member including a blade-shaped piece having a first threaded hole open at sides and a screw element brought into thread engagement with said first threaded hole, (c) leaving the implant member as fitted in the implanting groove over a specified period of time to allow a new growth of jawbone around the implant member, so that an osteobond develops between the jawbone portion and the exposed surface of the piece and the screw element, whereby a second threaded hole is formed along the exposed surface of the screw element, (d) subsequently forming a withdrawal hole extending outwardly from the top end of the screw element and releasing the screw element from thread engagement through the withdrawal hole, and (e) then bringing a threaded portion of a pin neck portion into thread engagement with said first and second threaded holes to mount the pin neck portion in position.

According to such contructional features of the invention, the screw element is brought into thread engagement with the first threaded hole of the piece, whereby it is possible to form an implant member having the threaded portion of the screw member exposed at two opposite sides of the piece. Just after extraction of a tooth, or some time after the extraction, a groove is cut along a jaw bone to form an implant groove, into which the integrated implant member is implanted, with the top end of the screw element about level with the surface of the jawbone, the implant member being left as it is for a period of time required to allow good osteobond (2 to 3 months). Thus, a second threaded hole continued to the first threaded hole of the piece is formed on the surface of a new bone growth. Subsequently, a mucous membrane is cut to release the screw element from the thread engagement. Then, the threaded portion of the pin neck portion is brought in thread engagement with the both threaded holes, whereby the pin neck portion is implanted in position.

Therefore, according to the invention, the implant member, as a piece, can be implanted in a limited area of jawbone structure in a stable manner and without detriment to adjacent natural teeth. About one half of the base end threaded portion of the pin neck portion can be fixed at the piece side, and the remaining some half portion exposed sidewardly of the piece can be firmly fixed on the jawbone side through good osteobond. Thus, stable implantation is assured. The base end threaded portion of the pin neck portion can be made reasonably thick within a certain permissible range, and accordingly sufficient strength can be assured against any substantial occlusa force. Futheremore, double implanting techniques can be effectively employed, it being thus possible to implant the piece in a post-extraction socket right after extraction of a number of teeth, with satisfactory osteobond effect.

BRIEF DESCRIPTION OF THE DRAWINGS

FIG. 19 is a longitudinal sectional view in front elevation showing the pin neck portion when brought in thread engagement;

FIG. 20 is a longitudial sectional view in side elevation thereof;

PREFERRED EMBODIMENTS

A first embodiment of the invention will now be described with reference to the accompanying drawings.

Figure 6:
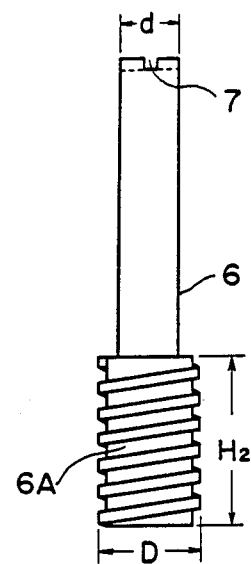
FIG. 6 is a front view of a pin neck portion according to the first embodiment of the invention.
Figure 1:
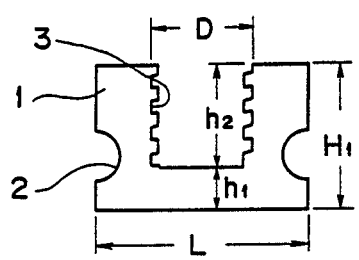
FIG. 1 is a front view of a piece according to a first embodiment of the invention.
Figure 4:
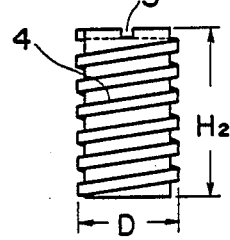
FIG. 4 is a front view of a screw element according to the first embodiment of the invention.
Figure 2:
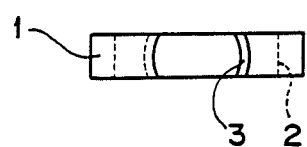
FIG. 2 is a plan view of the piece in FIG. 1.
Figure 5:
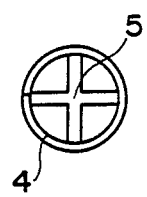
FIG. 5 is a plan view of the screw element in FIG. 4.
Figure 7:
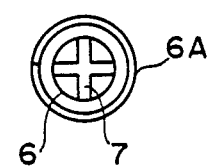
FIG. 7 is a plan view of the pin neck portion in FIG. 6.
Figure 3:
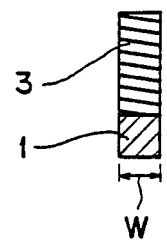
FIG. 3 is a longitudinal sectional side view of the piece in FIG. 1.

In FIGS. 1 to 3, numeral 1 designates a blade-shaped piece implantable in a jawbone, being approximately dimensioned, for example, as follows: height $H_1$, 7 mm; length L, 10 mm; thickness W, 2 mm. Two longitudinally extending sides of the piece 1 are each formed with a reces 2 for latch engagement with a jawbone. In the center of the piece 1 there is formed a first threaded hole 3 extending in the vertical direction and having a depth $h_2$ of about 6 mm, with a residual height $h_1$ of about 2 mm. This threaded hole 3 has a diameter D of about 5 mm. Accordingly, the piece 1 is open at two sides in the direction of its thickness, since the piece 1 is dimensioned about 2 mm in its thickness. In FIGS. 4 and 5, numeral 4 designates a screw element for formation of a threaded hole in a jawbone, which has a deameter D of about 5 mm so as to be engageable with the threaded hole 3. The screw element 4 is about 8 mm in its length $H_2$. The element 4 is formed at its outer end with a recess 5, such as for example a cross recess, for allowing a screw turning tool to act thereon. Referring to FIGS. 6 and 7, numeral 6 designates a pin neck portion threadedly engageable with the piece 1 for substitution for the screw member 4. The pin neck portion 6 has at its base end a threaded portion 6A integrally formed therewith and having same diameter D and same length $H_2$ as the screw member 4. At the outer end of the pin neck portion 6 there is formed a reces, such as for example a cross recess, for engaging of the screw turning tool. The diameter d of the pin neck portion 6, except that of the threaded portion 6A, is about 3 mm.

Above said piece 1 and pin neck portion 6 are made of a material having good strength and workability and which provides good osteobond or osteoadhesion with a jawbone, such as for example titanium, alumina ceramic, zircondia ceramic, or any composite of such material with sintered aphthite. The screw element 4 is made of a material having good workability, such as titatium, alumina ceramic, or zirconia ceramic.

Procedures for implanting an aritificial tooth root by using aforesaid member will be explained with reference to FIGS. 8 to 20.

Figure 10:
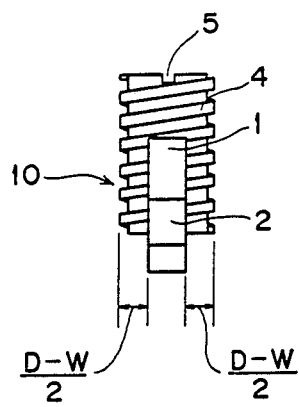
FIG. 10 is a side view of the implant member in FIG. 8.
Figure 8:
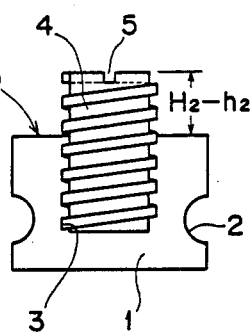
FIG. 8 is front view of an implant member according to the first embodiment of the invention.
Figure 9:
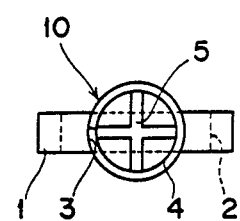
FIG. 9 is a plan view of the implant member in FIG. 8.

As shown in FIGS. 8 to 10, a screw element 4 is brought into thread engagemenet with the piece 4 to form an implant member 10. In this case, the screw element 4 exposedly projects laterally from both sides of the piece 1 by an amount corresponding to (D-W)/2, and also projects outwardly from the outer end of the piece 1 by an amount corresponding to ($H_2-h_2$)

Figure 11:
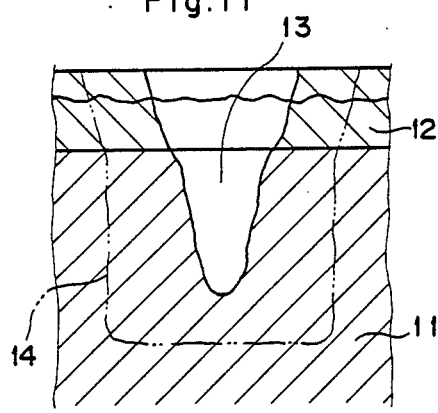
FIG. 11 is a longitudinal sectional view in front elevation showing a wound socket as it appears when a tooth is extracted.
Figure 13:
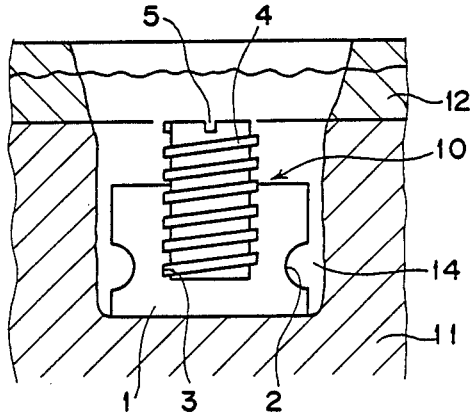
FIG. 13 is a longitudinal sectional view in front elevation showing the implant member as it appears when implanted in the socket.
Figure 12:
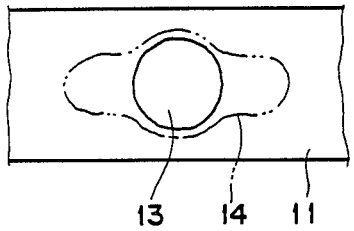
FIG. 12 is a plan view thereof.
Figure 14:
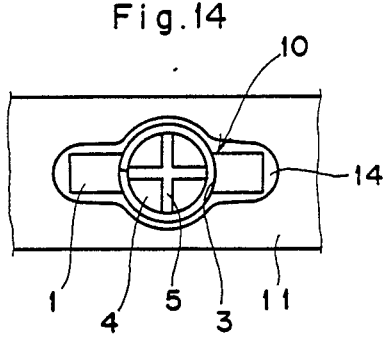
FIG. 14 is a plan view thereof.
Figure 15:
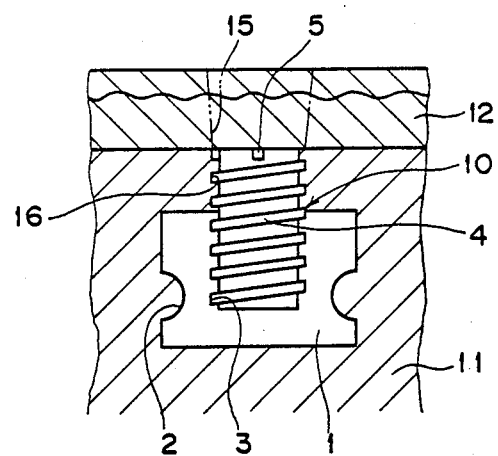
FIG. 15 is a longitudinal sectional view in front elevation showing a new growth of jawbone.
Figure 16:
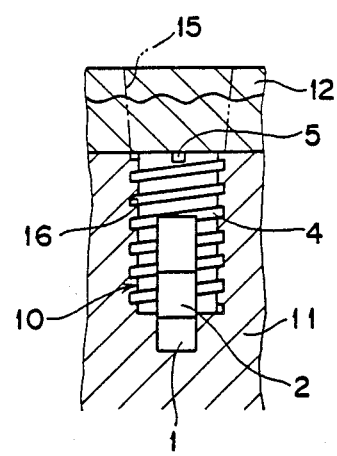
FIG. 16 is a longitudinal sectional view in side elevation thereof.

In a first series of procedures, as indicated in FIGS. 11 and 12 by solid lines, a groove is cut around a socket 13 formed over an area extending from a jawbone 11 to a nucous membrane 12 as a result of extraction of a natural tooth by using various pieces of equipment, whereby an implanting groove 14 is formed which is large enough to permit the implant member 10 to be fitted thereinto as indicated in FIGS. 11 and 12 by virtual lines. In the case where some time has passed after the tooth extraction and where no wound socket or no tooth in a jaw bank is present, a groove is cut in same way to form an implanting groove 14. Then, as shown in FIGS. 13 and 14, the implant member 10 is fitted into the implant groove 14 for mounting therein. This mounting is made at such level that the top end of the screw element 4 is scarcely exposed on the surface of the jawbone 11. In this condition, the implant member 10 is left as it is for a period of 2 to 3 months. In course of time, there is a new growth of jawbone around the implanting groove 14, with a bony surface formed along the screw element 4. Thus, as shown in FIGS. 15 and 16, good osteobond is formed on the exposed surface of the piece 1 and screw element 4.

Figure 17:
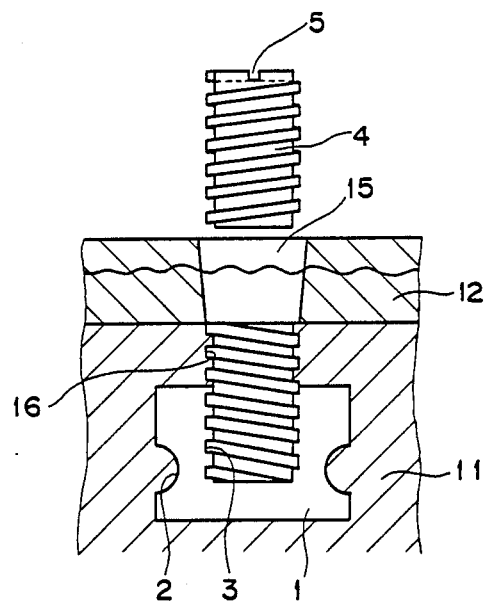
FIG. 17 is a longitudinal sectional view in front elevation showing the screw member when released from thread engagement.
Figure 18:
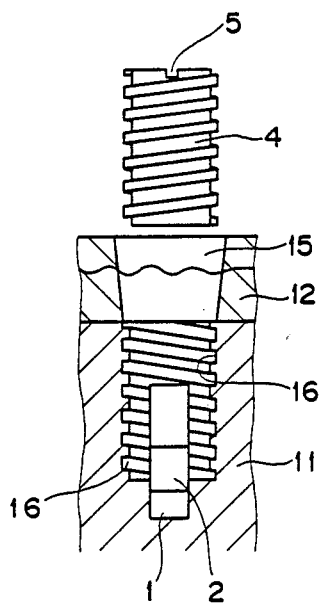
FIG. 18 is a longitudinal sectional view in side elevation thereof.

Subsequently, a second series of procedures is carried out. As shown in FIGS. 15 and 16 by virtual lines, the nucous membrane 12 is cut outwardly of the top end of the screw element 4 to form a withdrawal/insertion hole 15. The screw turning tool is applied to the recess 5 of the screw element 4 through the withdrawal hole 15 to disengage the screw element 4 in such manner as illustrated in FIGS. 17 and 18. As a result of this disengagement, a second threaded hole 16 is formed in the jawbone 11, said threaded hole 16 being in continuation to the first threaded hole 3 of the piece 1. Then the threaded portion 6A of the pin neck portion 6 is passed through the withdrawal/insertion hole 15 so that the threaded portion 6A is brought into engagement with the threaded hole 16 formed in the jawbone 11 and then with the threaded hole 3, as shown in FIGS. 19 and 20, whereby the pin neck portion 6 is implanted in position. Since the threaded hole 16 is already formed in the jawbone 11 and since the threaded hole 3 continued to the threaded hole 16 is present, such implanting can be readily and steadily performed through the jawbone 11 and into the piece 1. In connection with the implanting operation, a part of the threaded portion 6A is fixed to the piece 1 through the threaded hole 3 and the remaining portion thereof is fixed to the jawbone 11 by bone adhesion through the threaded hole 16. Subsequently, an upper crown 17 is prepared and fitted in position as shown in FIGS. 19 and 20 by virtual lines.

Figure 21:
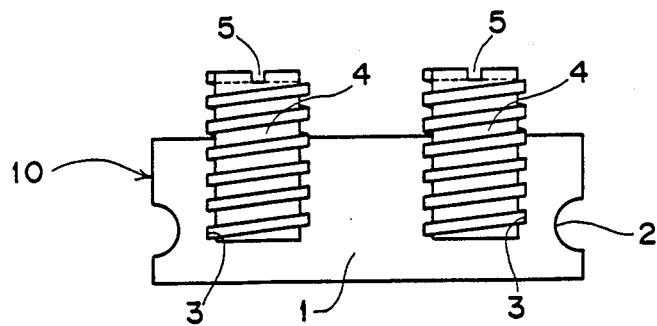
FIG. 21 is a front view showing an implant member according to a second embodiment of the invention.
Figure 22:
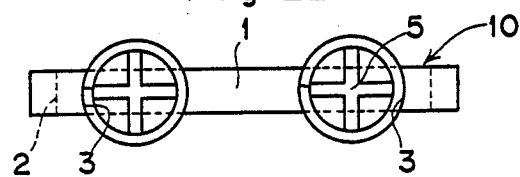
FIG. 22 is a plan view of the implant member in FIG. 21.
Figure 23:
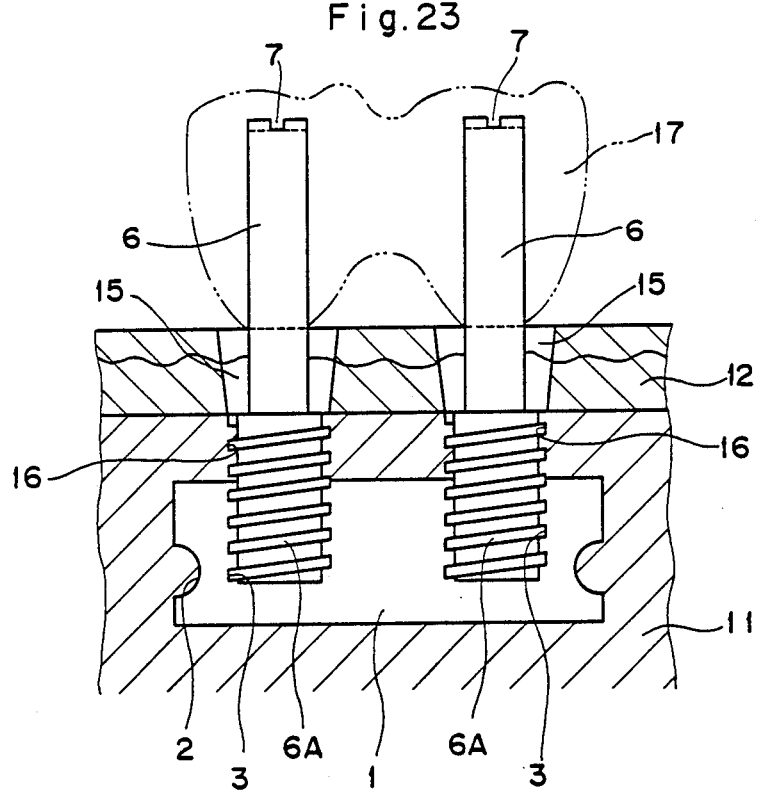
FIG. 23 is a longitudinal sectional front view of a pin neck portion when brought in thread engagement.

FIGS. 21 to 23 show a second embodiment of the invention, which is applicable in the case of a jawbone involving a large number of teeth lost or damaged. In this embodiment, two pin neck portions 6 are brought in thread engagement with one common piece 1, an upper crown 17 being fitted over the pin neck portions 6.

Figure 24:
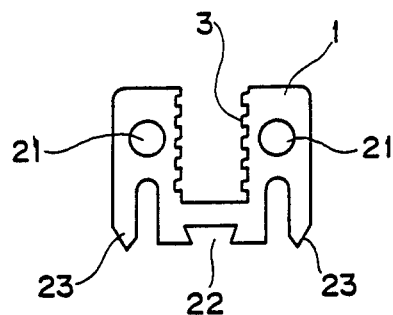
FIG. 24 is a front view of a third form of piece according to the invention.
Figure 25:
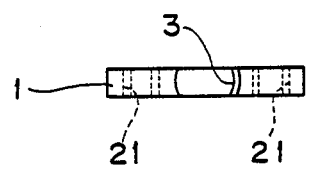
FIG. 25 is a plan view of the piece in FIG. 24.
Figure 26:
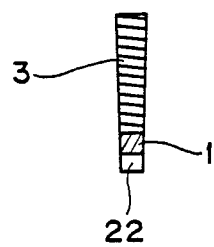
FIG. 26 is a longitudinal sectional view in side elevation of the piece in FIG. 24.

FIGS. 24 to 26 show a third form of piece 1 according to the invention. This piece 1 has a pair of through-holes 21, one on each side of the threaded hole 3, and a dovetail groove 22 at the bottom thereof. A jawbone growth develops with the through-holes 21 and the dovetail groove 22 for bony adhesion, whereby stronger bond between the jawbone 11 and the piece 1 can be obtained. The piece 1 is formed with a pair of blade edge portions 23, by means of which the insertion and driving of the piece 1 into the implanting groove 14 can be easily performed. As shown in FIG. 26, the piece 1 is so formed as to have a wedge-shaped sectional configuration. The insertion and friving of the piece 1 into the groove 14 can also be facilitated by such configuration.

Figure 27:
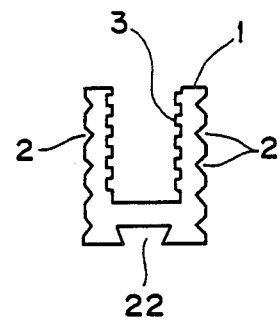
FIG. 27 is a front view of a fourth form of piece according to the invention.
Figure 28:
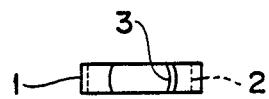
FIG. 28 is a plan view of the piece in FIG. 27.
Figure 29:
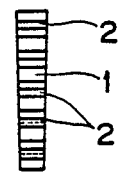
FIG. 29 is a longitudinal sectional view in side elevation of the piece in FIG. 27.

FIGS. 27 to 29 show a fourth form of piece 1 according to the invention. This piece 1 is formed on its both sides with a plurality each of recesses 2 in the longitudinal direction of the threaded hole 3. In this instance, the recesses 2 are each of a triangular configuration.

Figure 30:
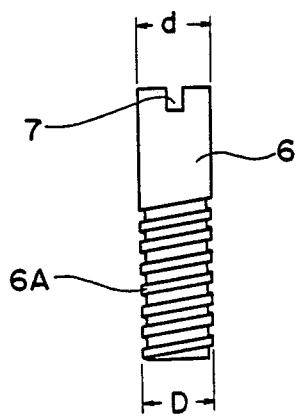
FIG. 30 is a front view of a second form of pin neck portion according to the invention.

FIG. 30 shows a second form of pin neck portion according to the invention. This piece 1, in its part other than the threaded portion 6A, has a diametral size d which is equal to the diameter D of the threaded portion 6A.

Figure 31:
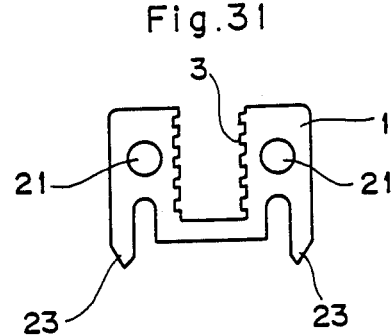
FIG. 31 is a front view of a fifth form of piece according to the invention.

FIG. 31 shows a fifth form of piece 1 according to the invention. This piece 1 is different from the piece 1 in FIGS. 24 to 26 in that it has no dovetail groove 22, but in other respects it is identical with the latter. Since no dovetail groove 22 is present, the blade edge portions 23 projects accordingly. Thus, the insertion and driving of the piece 1 into the implanting groove 14 can be further facilitated by the projecting edge portions 23.

Figure 32:
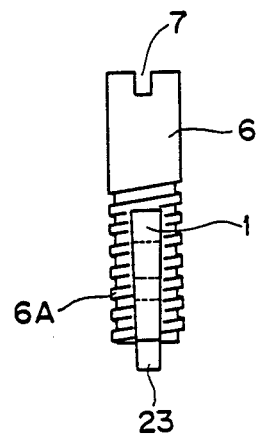
FIG. 32 is a side view of an artificial tooth-root member completed by bringing the pin neck portion in FIG. 30 into thread engagement with the piece in FIG. 31.

FIG. 32 shows pin neck portion 6 shown in FIG. 30 as it appears when in thread engagement with the piece 1 shown in FIG. 31. When in that condition, the pin neck portion 6 is implanted in a jawbone not shown.

Figure 33:
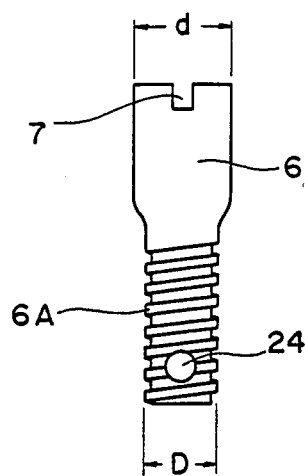
FIG. 33 is a front view of a third form of pin neck portion according to the invention.
Figure 34:
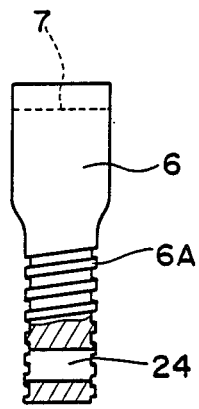
FIG. 34 is a side view of the pin neck portion in FIG. 33.

FIGS. 33 and 34 show a third form of pin neck portion 6 according to the invention. This pin neck portion 6, in its portion other than the threaded portion 6A, has a larger diameter d than the diameter D of the threaded portion 6A. On its end side, the threaded portion 6A is formed with a through-hole 24 extending in a radial direction of thereof. When the pin neck portion 6 is in thread engagement with the piece 1 in the jawbone 11, a new jawbone growth can develop within the through-hole 24 later and thus the threaded portion 6A can be positively fixed to the jaw bone structure.

Figure 35:
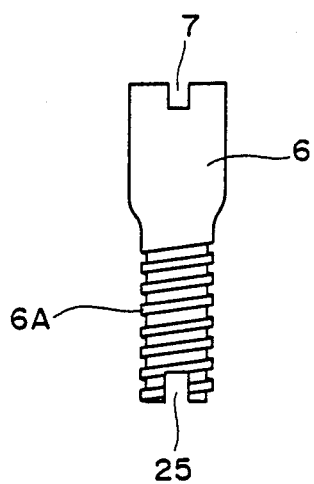
FIG. 35 is a front view of a fourth form of pin neck portion according to the invention.
Figure 36:
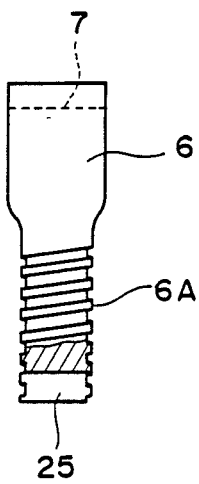
FIG. 36 is a side view of the pin neck portion in FIG. 35.

FIGS. 35 and 36 show a fourth form of pin neck portion 6 according to the invention. This pin neck portion 6 is formed at the end of the threaded portion 6A with a groove 25 for latch engagement with the jawbone 11, in place of the through-hole 24 of the pin neck portion shown in FIGS. 33 and 34.

What is claimed is:

1. An artificial tooth root member comprising a blade-shaped piece implantable in a jawbone and having a first threaded hole open at sides, a screw element threadedly engageable with the first threaded hole and serving for the purpose of forming a second threaded hole in the jawbone, and a pin neck portion substitutable for the screw element and formed at the base end part thereof with a threaded portion engageable with the first and second threaded holes.

2. An artificial tooth root member as set forth in claim 1, wherein said piece is formed with recess means for latch engagement with the jawbone.

3. An artificial tooth root member as set forth in claim 2, wherein said recess means is formed in plurality of recesses along the depth of the first threaded hole.

4. An artificial tooth root member as set forth in claim 2, wherein said recess means is in the form of a dovetail groove.

5. An artificial tooth root member as set forth in claim 1, wherein said piece is formed with a first through-hole for latch engagement with the jawbone.

6. An artificial tooth root member as set forth in claim 1, wherein said piece is formed with an edge portion which bites into the jawbone.

7. An artificial tooth root member as set forth in claim 1, wherein said piece is formed with a plurality of first threaded holes.

8. An artificial tooth root member as set forth in claim 1, wherein said piece is wedge-shaped.

9. An artificial tooth root member as set forth in claim 1, wherein the length of the screw element is greater than the depth of the first threaded hole.

10. An aritificial tooth root member as set forth in claim 1, wherein said screw element is formed with a portion to be acted upon by screw turning tool for tightening and loosening the screw element.

11. An artificial tooth root member as set forth in claim 1, wherein said pin neck portion is formed with a portion to be acted upon by a screw turning tool for tightening and loosening the pin neck portion.

12. An artificial tooth root member as set forth in claim 1, wherein the length of the threaded portion of said pin neck portion is greater than the depth of the first threaded hole.

13. An artificial tooth root member as set forth in claim 1, wherein the threaded portion of said pin neck portion is provided with a second through-hole extending radially of said threaded portion and latch-engageable with the jawbone.

14. An artificial tooth root member as set forth in claim 1, wherein the threaded portion of said pin neck portion is formed at the end thereof with a groove for latch engagement with the jawbone.

15. A method for mounting an artificial tooth-root member which comprises:
   (a) cutting a groove around a socket after tooth extraction to form an implanting groove,
   (b) fitting into the implanting groove an implant member including a blade-shaped piece having a first threaded hole open at sides and a screw element brougth into thread engagement with said first threaded hole,
   (c) leaving the implant member as fitted in the implanting groove over a specified period of time to allow a new growth of jawbone around the implant member, so that an osteobond develops between the jawbone portion and the exposed surface of the piece and screw element, whereby a second threaded hole is formed along the exposed surface of the screw element,
   (d) subsequently forming a withdrawal hole extending outwardly from the top end of the screw hole and releasing the screw element form thread engagement through the withdrawal hole, and
   (e) then bringing a threaded portion of a pin neck portion into thread engagement with said first and second threaded holes to mount the pin neck portion in position.

* * * * *